United States Patent
Oez (12)

(10) Patent No.: US 10,586,018 B2
(45) Date of Patent: Mar. 10, 2020

(54) METHOD AND SYSTEM FOR GENERATING A MEDICAL REPORT AND COMPUTER PROGRAM PRODUCT THEREFOR

(71) Applicant: Nuance Communications, Inc., Burlington, MA (US)

(72) Inventor: Mehmet M. Oez, Eindhoven (NL)

(73) Assignee: Nuance Communications, Inc., Burlington, MA (US)

(*) Notice: Subject to any disclaimer, the term of this patent is extended or adjusted under 35 U.S.C. 154(b) by 222 days.

(21) Appl. No.: 14/328,411

(22) Filed: Jul. 10, 2014

(65) Prior Publication Data

US 2014/0324477 A1 Oct. 30, 2014

Related U.S. Application Data

(63) Continuation of application No. 12/593,633, filed as application No. PCT/IB2008/051141 on Mar. 27, 2008, now Pat. No. 8,930,210.

(30) Foreign Application Priority Data

Mar. 29, 2007 (EP) .................................... 07105257

(51) Int. Cl.
*G16H 15/00* (2018.01)
*G06F 19/00* (2018.01)
(Continued)

(52) U.S. Cl.
CPC ........... *G06F 19/328* (2013.01); *G06Q 10/10* (2013.01); *G06Q 50/22* (2013.01); *G10L 15/265* (2013.01); *G16H 15/00* (2018.01)

(58) Field of Classification Search
CPC .... G06F 17/274; G06F 19/322; G06F 19/325; G06F 19/328; G06F 19/3406
(Continued)

(56) References Cited

U.S. PATENT DOCUMENTS 5,051,924 A 9/1991 Bergeron et al.
6,514,201 B1 * 2/2003 Greenberg ........... A61B 5/7475
600/437
(Continued)

OTHER PUBLICATIONS

"CSS Properties: Display vs. Visibility"; Kurt cagle; Jan. 5, 2000; devX.com.*
(Continued)

*Primary Examiner* — John A Pauls
(74) *Attorney, Agent, or Firm* — Wolf, Greenfield & Sacks, P.C.

(57) ABSTRACT

A method and a system for generating, with the assistance of a computer system (12), a medical report (18) suitable for automatic billing, where an electronic template (39) suited for a specific patient's condition is selected out of a plurality of given electronic templates stored in storage means (15); personal data of the specific patient's and previously stored in storage means (11) are automatically entered into the selected electronic template; and medical report text passages and instructions are entered into the selected template by dictating and using a speech recognition system (13); additionally, condition data are automatically entered on the basis of condition information as far as stored in storage means (7) into the selected template, and code data associated with these condition information are automatically embedded in the selected template; and when entering medical report text passages, at least one predetermined voice macro stored in the storage means (16) together with code data embedded therein is called in; the code data thus embedded in the medical report (18) being applicable when coding the medical report for automatic billing.

20 Claims, 4 Drawing Sheets

(51) Int. Cl.
  *G06Q 10/10*  (2012.01)
  *G06Q 50/22*  (2018.01)
  *G10L 15/26*  (2006.01)
(58) Field of Classification Search
  USPC .............................. 705/2, 3; 600/179, 437
  See application file for complete search history.

(56) References Cited

U.S. PATENT DOCUMENTS

| | | | |
|---|---|---|---|
| 6,813,603 | B1 | 11/2004 | Groner et al. |
| 6,819,785 | B1 | 11/2004 | Vining et al. |
| 2002/0082825 | A1* | 6/2002 | Rowlandson ......... G06F 17/274 704/9 |
| 2002/0131625 | A1 | 9/2002 | Vining et al. |
| 2002/0147615 | A1* | 10/2002 | Doerr ................... G06F 19/325 705/2 |
| 2003/0083577 | A1 | 5/2003 | Greenberg |
| 2004/0128163 | A1* | 7/2004 | Goodman ........... G06F 19/3406 705/2 |
| 2004/0172296 | A1* | 9/2004 | Wohl ................... G06F 19/322 705/2 |
| 2004/0220895 | A1* | 11/2004 | Carus ................... G06F 19/322 |
| 2004/0254816 | A1 | 12/2004 | Myers |
| 2005/0197536 | A1 | 9/2005 | Banik et al. |
| 2005/0197547 | A1 | 9/2005 | Trinks et al. |
| 2006/0041428 | A1 | 2/2006 | Fritsch et al. |
| 2006/0212452 | A1 | 9/2006 | Cornacchia |
| 2006/0277073 | A1 | 12/2006 | Heilbrunn et al. |
| 2007/0050187 | A1* | 3/2007 | Cox ....................... G06F 19/328 704/9 |
| 2008/0077443 | A1* | 3/2008 | Singer .................. G06F 19/322 705/3 |
| 2008/0147436 | A1* | 6/2008 | Ohlsson .............. G06Q 10/087 705/2 |
| 2010/0114598 | A1 | 5/2010 | Oez |

OTHER PUBLICATIONS

European Office Action from the European Patent Office for Application No. 08719854.5 dated Mar. 16, 2012.
International Search Report for Int'l Application No. PCT/IB2008/051141, dated Aug. 19, 2008.
Written Opinion of the Int'l Searching Authority for Int'l Application No. PCT/IB2008/051141, dated Aug. 10, 2008.
Kyrnin, What is XML? About.com. Downloaded Sep. 22, 2011. 2 pages.
Summons to Attend Oral Proceedings for EP Application No. 08719854.5 dated Jun. 1, 2016.
EP 08719854.5, Nov. 14, 2016, European Communication.
EP 08719854.5, Dec. 16, 2016, European Communication.
European Communication for European Application No. 08719854.5 dated Nov. 14, 2016.
European Communication for European Application No. 08719854.5 dated Dec. 16, 2016.

* cited by examiner

METHOD AND SYSTEM FOR GENERATING A MEDICAL REPORT AND COMPUTER PROGRAM PRODUCT THEREFOR

CROSS-REFERENCE TO RELATED APPLICATIONS

This application is a continuation of U.S. patent application Ser. No. 12/593,633, entitled "METHOD AND SYSTEM FOR GENERATING A MEDICAL REPORT AND COMPUTER PROGRAM PRODUCT THEREFOR," filed on Sep. 29, 2009, which is incorporated herein by reference in its entirety. U.S. patent application Ser. No. 12/593,633 is a U.S. National Stage entry of International Application Serial No. PCT/IB2008/051141, entitled "METHOD AND SYSTEM FOR GENERATING A MEDICAL REPORT AND COMPUTER PROGRAM PRODUCT THEREFOR," filed on Mar. 27, 2008, which claims priority to European Patent Application No. 07105257.5, entitled "METHOD AND SYSTEM FOR GENERATING A MEDICAL REPORT AND COMPUTER PROGRAM PRODUCT THEREFOR," filed on Mar. 29, 2007.

FIELD OF THE INVENTION

The present invention relates to a method for generating, with the assistance of a computer system, a medical report suitable for automatic billing, said method comprising:

selecting an electronic template suited for a specific patient's condition out of a plurality of given electronic templates stored in storage means;

automatically entering personal data of the specific patient as previously stored in storage means, into the selected electronic template; and entering medical report text passages into the selected template by dictating and using a speech recognition system.

Furthermore, the invention relates to a system for generating a medical report suitable for automatic billing, said system comprising:

storage means for storing personal data;

storage means for storing condition information of patients;

storage means for storing a plurality of predetermined electronic templates;

means for selecting an electronic template suited for a specific patient's condition;

means for automatically entering personal data of the specific patient as stored in the storage means into the selected electronic template; and means for entering medical report text passages into the selected template by dictating and using a speech recognition system.

Moreover, the invention concerns a computer program product comprising a computer-readable medium bearing computer executable instructions for carrying out such a method for generating a medical report.

BACKGROUND OF THE INVENTION

In the field of medical healthcare, it is usual to generate medical reports where a respective physician dictates the report to generate a speech file in a computer system, which speech file is then automatically converted into a text file by using a speech recognition system; the transcribed text file usually is manually corrected and checked to create the final medical report document.

After a medical report is completed, it is often necessary, or even prescribed, that the report "is coded" according to strict guidelines so that e.g. an insurance company or a government organization can be billed for payment. Each type of medical service provided, prescriptions made, referrals cited must be identified from the report text itself accordingly. The coding guidelines are strict and very complex.

Delivering quality healthcare depends on capturing accurate and timely medical data. Medical coding professionals fulfill this need as key players in the healthcare workplace.

At present, health information coding is the transformation of verbal descriptions of diseases, injuries, procedures etc., generally referred to as "condition information" in this context, into numeric or alphanumeric designations. Originally, medical coding was performed to classify mortality (cause of death) data on death certificates. However, coding is also used to classify morbidity and procedural data. The coding of health-related data permits access to medical records by diagnoses and procedures for use in clinical care, research, and education.

Since the implementation of automatic billing on the basis of coded medical reports, there has been much more emphasis placed on medical coding. Currently, reimbursement of hospital and physician claims for medicare patients depends entirely on the assignment of codes to describe diagnoses, services, and procedures provided. To overcome the problem of healthcare fraud and abuse, as the basis for reimbursement, appropriate and accurate medical coding has become crucial as healthcare providers seek to assure compliance with official coding guidelines.

There are many demands for accurately coded data from the medical record. In addition to their use on claims for reimbursement, codes are included on data sets used to evaluate the processes and outcomes of healthcare. Code data are also used internally by institutions for quality management activities, case-mix management, planning, marketing and other administrative and research activities.

Currently, the coding process is either manual, or it is done in an extra processing step semi-automatically using a text parsing tool (also using a "natural language processing" ("NLP") or "semantic web" technology), compare for instance U.S. Pat. No. 6,915,254 B1 where a system for automatically assigning medical codes using NLP is described. Of course, manual coding is very cumbersome and lengthy and expensive, since properly trained coding personnel is very scarce. On the other hand, the text parsing system using NLP is error prone since it has to analyze human readable text, which is often vague. Additionally, it is to be considered that there is a shortage of certified medical coders in hospitals, physician practices, and other healthcare facilities. According to the United States Bureau of Labor, employment of medical record and health information technicians is expected to grow much faster than the average field.

From US 2003/0154085 A1, it is already known to use predetermined electronic templates to be filled out when generating medical reports under the assistance of computer means. In particular, a specific, suitable template apt for the specific patient and his condition is selected by the physician, and personal data of the respective patient, as name, address, age, sex etc., are automatically inserted into this template, such personal data being already available from a hospital information system (HIS). Then, the physician dictates his specific text using an interactive voice interface of the computer system, for describing a particular diagnosis, procedure, medication etc., as appropriate. This speech file is automatically converted into a text file by speech recognition.

During dictation, the system compares the speech input with predetermined terms or phrases stored in a database, to match the audio input with such terms and phrases, that is to determine whether the audio input would be apt for later automatic NLP coding; in the case of a lack of match, the physician is requested to repeat or clarify his audio input, to arrive at a match.

Apparently, also this prior art system is cumbersome, lengthy and expensive.

SUMMARY OF THE INVENTION

It is an object of this invention to improve the report generation as well as the post-processing step with respect to coding the report, by using explicit information already available while creating the report using keywords.

According to a first aspect, the present invention provides a method for generating, with the assistance of a computer system, a medical report suitable for automatic billing, said method comprising:

selecting an electronic template suited for a specific patient's condition out of a plurality of given electronic templates stored in storage means;

automatically entering personal data of the specific patient's and previously stored in storage means into the selected electronic template; and entering medical report text passages and instructions into the selected template by dictating and using a speech recognition system;

wherein condition data on the basis of condition information as far as stored in the storage means are automatically entered into the selected template, and code data associated with these condition information are automatically embedded in the selected template; and when entering medical report text passages, at least one predetermined voice macro stored in storage means together with code data embedded therein called in;

the code data thus embedded in the medical report being applicable when coding the medical report for automatic billing.

According to a second aspect, the invention provides a system for generating a medical report suitable for automatic billing, said system comprising:

storage means for storing personal data;

storage means for condition information of patients;

storage means for storing a plurality of predetermined electronic templates;

means for selecting an electronic template suited for a specific patient's condition;

means for automatically entering personal data of a specific patient as stored in the storage means into the selected electronic template; and means for entering medical report text passages into the selected template by dictating and using a speech recognition system;

wherein the system further comprises means for automatically entering condition data on the basis of condition information of the specific patient as far as stored in the storage means into the selected template, and for automatically embedding code data associated with these condition information in the selected template; and storage means for storing predetermined voice macros having code data embedded therein, at least one of said voice macros together with code data being called in when entering medical report text passages;

the code data thus embedded in the medical report being applicable when coding the medical report for automatic billing.

Then, in accordance with an third aspect of the invention, there is provided a computer program product comprising a computer-readable medium bearing computer executable instructions for carrying out the method according to the invention.

The present invention is based on the fact that the respective report generation system or tool which is used to create the electronic medical report document is usually connected to an imaging station (PACS—picture archiving and communication system) and/or the RIS/HIS system of the hospital, so that it knows what kind of image or examination or visit is being reported (i.e., for instance, ultrasound of the kidney, MRI (magnetic resonance image) of the brain, CT (computer tomography) scan of the spine etc). Also, by using the specific location in the selected template as called in for dictating, the report generation tool knows what is being dictated (for instance, discharge summary, medication/prescriptions, measurements and units and what type etc). Therefore, it is possible to combine information from the RIS/HIS/PACS about examinations, images, procedures; information from the report text (voice macro) during dictation (speech recognition) about procedure, medications, prescriptions, allergies etc., as well as about which images were relevant etc., and to embed corresponding code data immediately in the report being generated, in particular with the use of hidden tags (e.g. xml-based).

All these code data can be passed then to the post processing step for coding, without any loss of accuracy due to inference or guessing, so that the overall accuracy of the system will be improved. The information can also be fed back to the speech recognition (SR) engine to improve recognition accuracy thereof, so the benefit is in both directions.

In the post processing step, the code data embedded in the respective medical report can be checked, and if necessary, can be converted in prescribed final code data unless the embedded code data are the prescribed code data. Furthermore, in this coding step, possible ambiguities still present can be cleared automatically or manually in a manner as known per se.

However, it should be mentioned here that the present invention makes it possible to check the code data already at the side of the physician dictating the medical report; here, possible ambiguities as to the code data in the dictated medical report may be ruled out automatically by checking the patient's personal data, as for instance sex, age, and excluding code data which are not consistent with such personal data. Thus, it is possible to exclude for instance code data as to a prostate issue for a female patient, or breast cancer for a male patient. Furthermore, possible ambiguities can be ruled out by automatically checking previous condition information, for instance with respect to an earlier examination result confirming high cholesterol so that now, a specific heart condition is likely. Furthermore, the actual medical examination information as established by the physician can be used, too, to rule out possible ambiguities as to the code data; for instance it is not necessary to include neurology codes in the case that the examination refers to a chest X-ray imaging or the like.

The code data may be linked to the respective condition information, as for instance CT images, X-ray images, MRI-images and so on, already during creation of said images, or such code data can be assigned to such images at the site of the physician, when examining such images, where the code data can be assigned automatically on the basis of the type of the images, too. Then, by the use of voice macros having code data, too, embedded therein, it is possible to embed further code data in the medical report automatically by calling in or downloading such voice macros.

The code data can be embedded in the medical report with hidden tags so that, when the medical report is e.g. printed or viewed on a terminal display, only the text of the medical report can be seen whereas at the post processing step, the code data which are embedded in the medical report, and are hidden for the human eye, may be checked, or converted in the final code data, if so provided.

Thus, advantageously, a method and system as well as a computer program product for computer-aided generation of medical reports are provided which allow for automatic "coding" in a highly efficient, time-saving and accurate manner. Further the invention makes use of the given resources available in a HIS (hospital information system) or RIS (radiology information system) or the like, in a hospital's computer system, to obtain accurate code data.

BRIEF DESCRIPTION OF THE DRAWINGS

The invention will be further explained now with reference to preferred embodiments to which, however, the invention should not be limited, and on the basis of the attached drawings in which.

DETAILED DESCRIPTION

Figure 1:
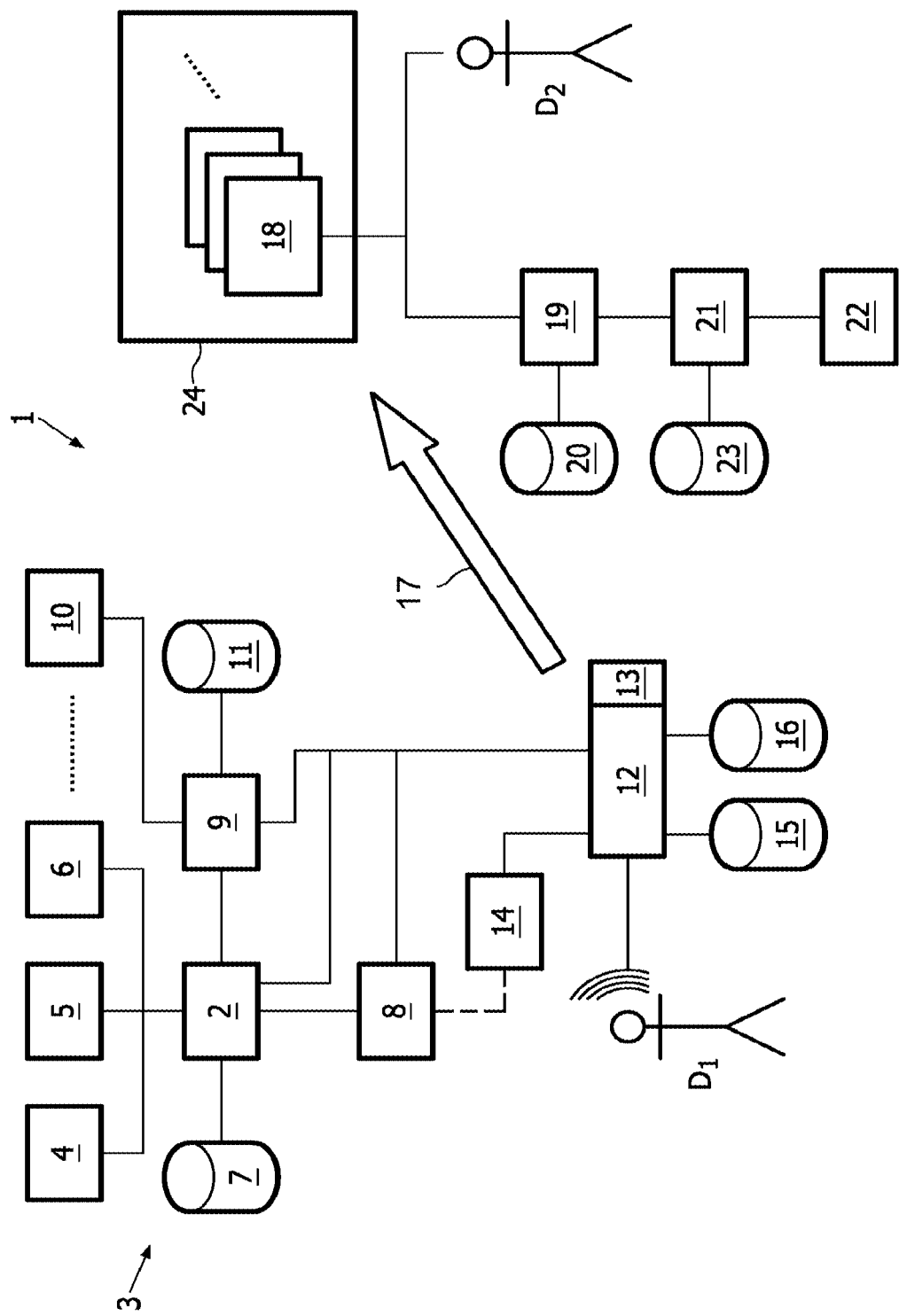
FIG. 1 shows a schematic block diagram illustrating a system, or a method, respectively, for generating a medical report in accordance with an embodiment of the invention.

FIG. 1 shows a schematic block diagram illustrating a system 1 for generating a medical report based on medical images of a patient according to a preferred embodiment of the invention. Modern medical information systems use so called picture archiving and communication systems ("PACS") for storing, observing and analyzing images obtained in medical applications. Such a PACS 2 is shown in FIG. 1 as a part of a computer system 3, and is used with several technologies for observing the interior anatomy of a human being. Imaging systems may include X-ray equipment or radiography 4, ultrasound equipment 5, computer tomography equipment 6 and/or other imaging systems (not shown), such as magnetic resonance imaging (MRI), position emission tomography, mammography or endoscopy. Different images of a patient or of parts of a patient are stored in a database 7 as storage means of the PACS 2.

Usually, the PACS 2 comprises a sewer which e.g. is connected to clients 8 (only one client 8 being shown in FIG. 1) which provide or utilize the images. The PACS 2 is connected to a radiology/hospital information system (RIS/HIS) 9 having associated therewith input means 10 and storage means 11 which contain additional information about the patients, namely, in particular personal (demographic) data, order information, exam information and the like.

A physician, particularly a radiologist $D_1$, uses the client computer 8 for viewing the images of a respective patient during generation of a medical report. The author of the medical report, particularly a radiologist. $D_1$, further uses a dictation system 12, e.g. a PC, a notebook, a laptop or the like computer comprising a usual speech recognition tool or system 13 for generation of the medical report. During generation of medical reports the radiologist $D_1$ is examining images on the screen of at least one client 8 of the PACS 2. When dictating the medical report, the radiologist or physician $D_1$ may effect inputting of such images to his computer or dictation system 12, generally entering of condition data which are received from the PACS 2. Here, such condition information, in particular X-ray images, US-images, CT-images, MRI-images or the like, have already linked thereto electronic code data, and usually, such condition information together with associated code data is already stored in the storage means 7. In the case that code data are still missing in connection with such condition information, it is possible to automatically assign such code data to the condition information on the client 8 via the computer 12 through a code assigning unit 14 (which may be part of the computer/dictation system 12, too). It should be mentioned that this code assigning unit may be part of computer or dictation system 12 or of the client computer 8, as it would be apparent to persons skilled in the art.

Furthermore, computer 12 is connected to storage means 15 having stored therein predetermined templates for respective types of medical reports, depending on the respective condition 5, as well as storage means 16 for voice macros (text blocks) which may be used as part of the text of the medical report to be established by the physician or radiologist $D_1$ by means of the computer 12. Such templates and such voice macros have been established previously, and may be selected in accordance with a respective patient and the respective condition, thus in accordance with a medical report to be generated. Accordingly, the physician $D_1$ can "trigger" the certain template, for example a template for a mammogram, and he/she can further use suited voice macros apt for this purpose. The templates have various areas or locations for the specific text and data ports, as will be explained below in more detail by way of example. The voice macros again have code data embedded therein which may be used for automatic billing, as will be explained below in more detail, too.

During dictation using the dictation system 12, the speech file is automatically converted to written text by means of the speech recognition system 13, and as schematically shown at 17 in FIG. 1, a transcriptionist may correct the report and send the report back to the author, particularly to the radiologist $D_1$, for review. After possible corrections, the reporting radiologist $D_1$ finally signs the corrected report and the final report 18 is stored and delivered. A referring practitioner $D_2$ or the respective patient receives the final report 18, for instance by mail, by fax, or via Internet, by using a terminal being connected to the system where the final reports 18 are stored, e.g. the system 1.

As mentioned, the final report 18 has to be provided with special codes e.g. for billing purposes, usually demanded by an insurance company. In general, coding can be done manually or computer-assisted in a coding system 19 having database means 20 connected thereto. Within a billing system 21 the invoices are generated and sent to an insurance company 22, to the patient etc. The generated billing documents can be stored in a database 23 being connected to the billing system 21.

The coding system 19 is often separate from the system 1, but can receive the medical reports 18 with the code data which have already been embedded therein during generation of the report at the site 12. The code data embedded in the respective medical reports may already be the final codes or code data, as prescribed, or may be temporary code data which are converted into the final codes at the coding system 19, by using tables or the like stored in the database means 20.

With a system as shown in FIG. 1, the following work flow when generating a medical report may be established.

At the beginning, the patient is admitted to hospital, and a patient record is created or updated using input means 10 to the RIS/HIS computer system 9, and the respective patient's personal data are stored in database means or storage means 11. Furthermore, an initial consultation or diagnosis may be carried out or established, and the results thereof are again stored in storing means 11.

Then, the patient moves to the relevant department, as for instance radiology, orthopaedy or the like, and if needed for further diagnosis, the patient is sent to some imaging department, as for instance, radiology department, for producing a corresponding image. This order is again inputted to computer 9 and stored in database means 11.

The patient is then received in the technical—radiology or the like—department, and there, the requested image (e.g. X-ray, see radiography station 4; ultrasound see station 5; CT, see station 6, etc.) is produced, and a corresponding examination report is created. Thereafter, these examination results are designed to a specific physician, for instance the physician $D_1$ in FIG. 1, in the radiology department, There, the physician $D_1$ receives the images over the PACS system 2 (server) and the client 8, or in film form, and he/she studies these images as well as the further information received from the RIS/HIS computer 9 with respect to personal data, previous condition information or the like. The physician $D_1$ then starts to read the study, and dictates the medical report to the digital dictation system or computer 12 comprising speech recognition. As explained, usually a transcriptionist then corrects the report and sends it back for review. The corrected report is signed by the physician $D_1$ and is delivered as final report 18. The final reports 18 are stored in storage (database) means 24 which may also be a part of the hospital's database.

In the past, coding took then place after this stage in the coding system 19. There were two ways to carry out the coding, namely the manual way where a coding specialist read the final report text and coded it, and the computer-assistant coding where the report text was fed to a software program which analyzed the text using complex algorithms (based on NLP, semantic nets or similar).

According to the invention, to minimize human involvements, and to make the final result more accurate, it is intended not to use just the report text for the evaluation and coding but to gather all available information possible in a previous stage, namely during the dictation of the report or still more previously. As may be seen from FIG. 1 and the description given above, there is much information already available from the beginning, when the patient is admitted to the hospital, and corresponding personal data and the like are entered in the system 1, the production of images, until dictation of the medical report, and that information is available electronically in the system 1.

This information first includes patient's personal data, which may be used as hints to rule out ambiguities the system may run into when assigning code data. This data can be:

patient's sex (to rule out possibilities e.g. for a prostate issue for a female patient, or breast cancer for a male patient)

previous conditions (it is more likely to be dealing with a heart condition if a previous condition is high cholesterol etc.)

exam information: there is no need to include urology codes if the exam is of the chest or the left arm, or MRI of the brain.

More importantly, the combination of all this information can help very much; for example; a patient is a 65 year old male with high cholesterol, and the exam is of the chest, with family history of heart issues—it is then very much likely that there is a heart condition, but no breast cancer condition.

Another source of information is the report generation tool. With the present system 1, the doctor does not dictate into a clean sheet, but uses a pre-prepared suited electronic template which is selected, and uses generally automated voice macros to aid reporting.

More in detail, depending on the exam and diagnosis, the doctor can "trigger" a certain template for the report. As an example, for a mammogram, the doctor (or the system, depending on configuration) can generate a report template (outline) that looks like this:

<patient information from the system>
<exam information from the system>
Procedure: X-Ray of the breast
Previous History: <information from the system>
[ . . . ]
Clinical Statement: [ . . . ]
Findings: [ . . . ]
Impression: [ . . . ]
Medications: [ . . . ]
<attending doctor's information from the system>
<hospital information from the system>
<billing information>

All the doctor has to do is to dictate between the brackets, [ . . . ]. Here, he may use voice macros to fill in the text between the brackets.

From the report template, and also from the voice macros, the system knows when the doctor is dictating a previous condition (if he is dictating under "previous history") or when he is prescribing medication (if he is dictating under "medications"). The main diagnosis is most likely under the section "impression" or "findings".

All this information is available to the report generation tool, which also knows when a specific section of the report begins and ends.

In addition, another source of information is, with almost negligible effort in configuration, to "embed" explicit coding information in the voice macros the doctor is using. For example, if the code for a category-2 breast exam is XYZ0000142, with a recommended follow-up exam coded XYZ2000144, and a prescribed medicine YYYY with code XYT0000454-->, this code information can be embedded explicitly to the voice macro with a hidden tag (xml-based) and can be made available without parsing or any other algorithms.

Figure 2:
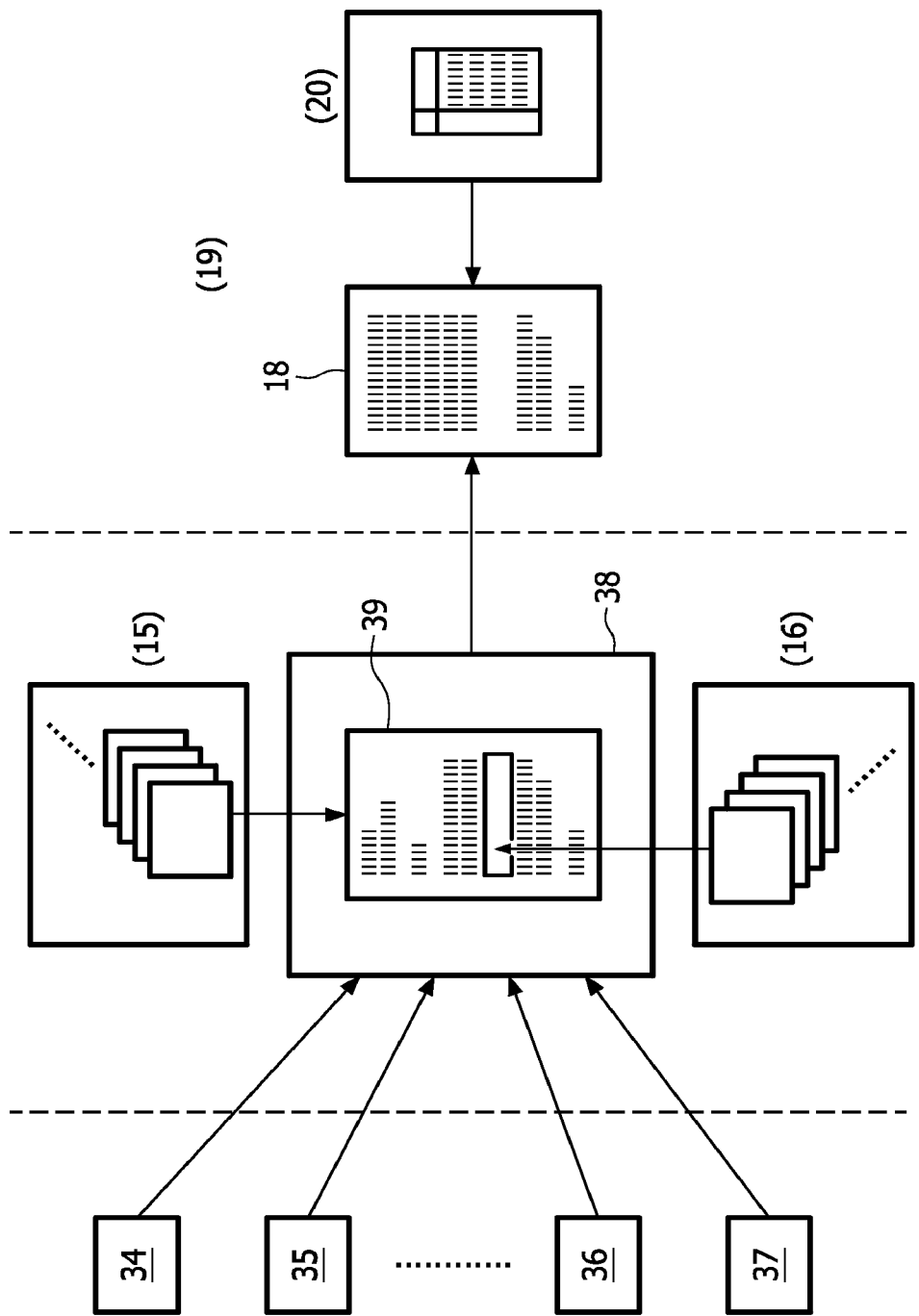
FIG. 2 shows a schematic work flow diagram illustrating processing steps at different locations or at different times, when establishing the medical report and coding it.

This way of processing is also illustrated in the schematic illustration of FIG. 2 where different areas or stations 31, 32 and 33 (31—HIS/RIS/PACS; 32—report generation; 33—coding station) or shown. For instance, FIG. 2 shows at block 34 that patient data are entered or updated in the HIS/RIS computer 9 by using imputing means 10 and are available thereafter in the system 1, that is, corresponding demographic infos, as name, sex, age, as well as previous info, as exams, conditions, diagnosis, medications, are stored then in storage means 11, and may be read out from there.

It should be mentioned that general storage means are possible which may comprise at least the storage means 11 and 7, preferably also storage means 15 and 16, as mentioned above in connection with FIG. 1. Furthermore, initial consultation is done at the side of the HIS/RIS computer 9, and the result is entered using imputing means 10; and is stored in storage means 11.

Then, the processing steps at a special center follow, e.g. in the radiology department or the like as illustrated, and procedure details as well as detailed diagnosis data and images are stored in storing means 7, compare blocks 35, 36 in FIG. 2.

During production of images, preferably, the respective code data are directly assigned.

Finally, block 37 refers to previous examination information as may be gathered again from storing means 11 through computer 9.

At station 32 of FIG. 2, the medical report is generated, as is schematically illustrated at block 38. Here, the personal or demographic data of the patient are downloaded, and the necessary data are automatically filled in, as far as necessary, in a specific template 49 which has been selected from the plurality of electronic templates as stored in storage at database means 15 in FIG. 1. Furthermore, image information as received from blocks 35, 36, in particular, in combination with code data already assigned thereto, are transmitted to the client 8, and, as far as necessary, are transmitted to the computer 12 of the physician $D_1$, so that the necessary data can be filled in into the selected template 49, too.

Moreover, previous exam information as taken at 37 may be used, too, to fill in the selected template 39. Then, as far as still necessary, text is dictated by the physician $D_1$ thereby using one or more voice macros as stored in storage (database) means 16. Also here, code data embedded in the voice macros are, additionally, transferred to the selected template 39, and are embedded therein with hidden tags.

Accordingly, the medical report as generated now already includes all or almost all necessary codes which are used later for billing purposes or the like. The codes can be final codes, as mentioned above, which allow direct use when billing the care done in the hospital. As an alternative, the code data embedded in the final medical report 18 may be temporary code data.

At station 33, final coding is then performed by using the prescribed codes, e.g. as stored in database means 20, e.g. in tables so that specific code can be assigned to temporary code data embedded in medical report 18.

Figure 3:
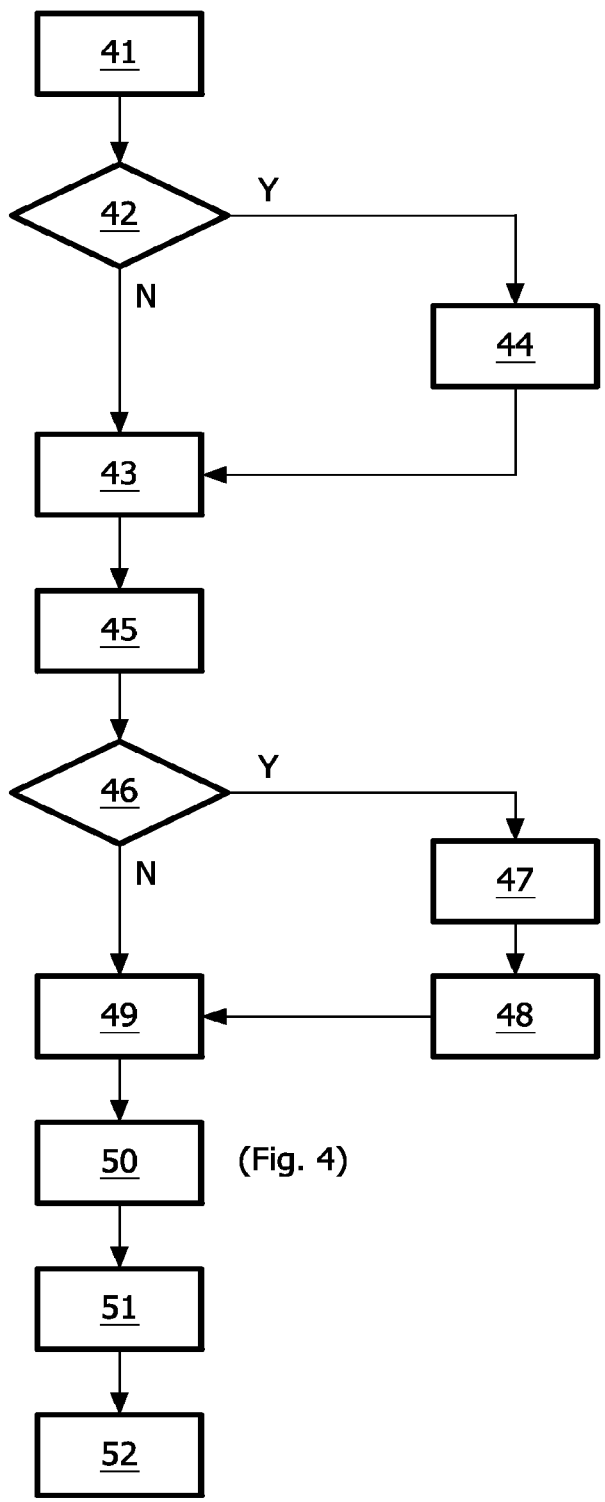
FIGS. 3 and 4 illustrate a general flow chart (FIG. 3) and a detailed part of this flow chart (FIG. 4), to show the establishment of a medical report having code data embedded therein.
Figure 4:
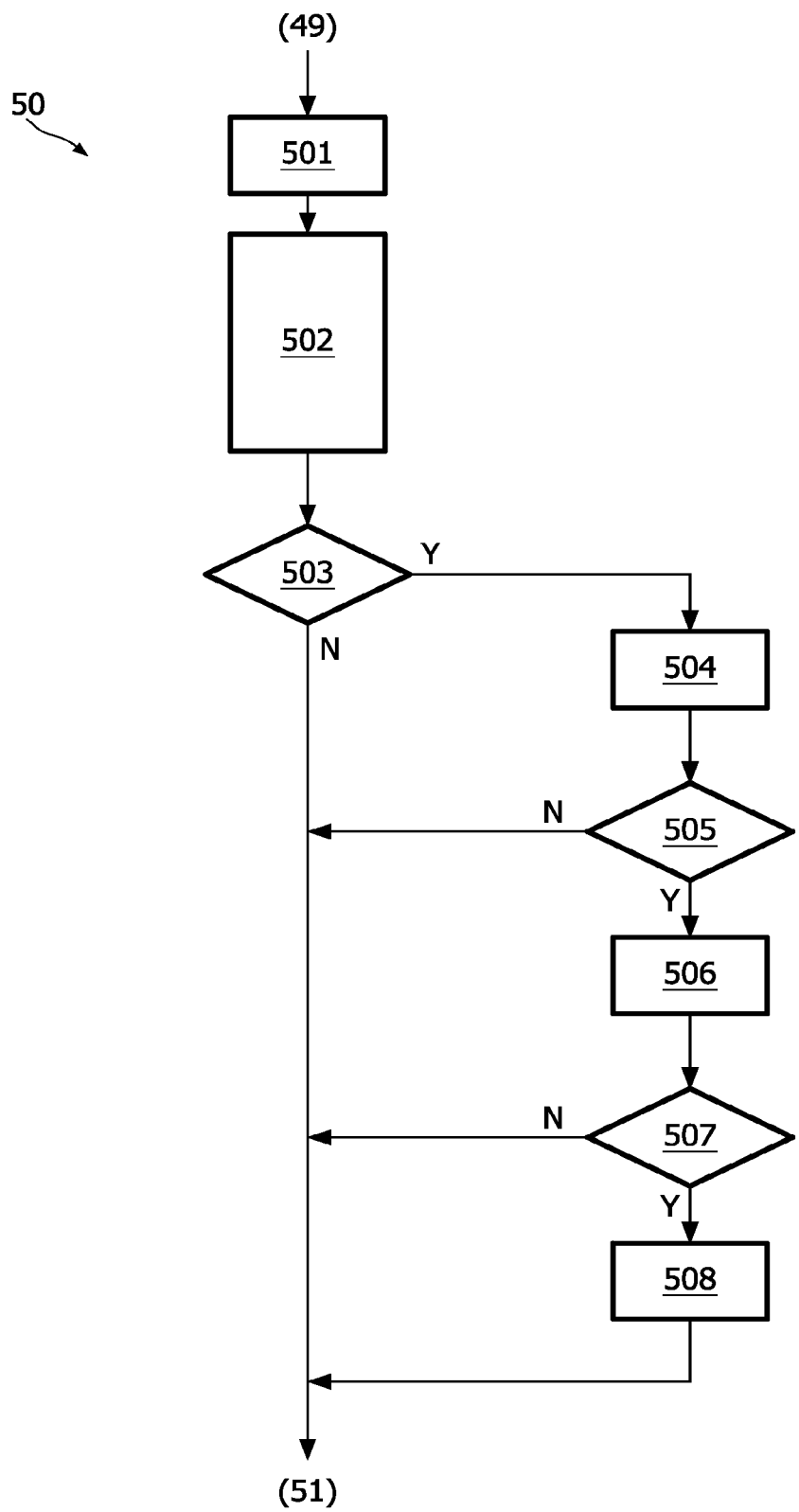

In FIG. 3, a general flow chart is shown to illustrate the process of generating a medical report, beginning with the arrival of a patient at the hospital or a care center, compare block 41 in FIG. 4. According to block 42, it is then checked whether the patient is a new patient, that is whether there are new personal data to be inputted with respect to this patient (path "Y"), or whether the patient is an already registered patient, and no amendment of personal data is necessary (path "N"). In the latter ease, the patient is sent to the place for carrying out initial consultation etc., compare block 43 in FIG. 4. This initial consultation etc. includes for instance general medical condition determination, question of complaints, establishment of clinical statements and initial diagnosis etc. In the case that the patient is a new patient, or that the personal data are to be amended, such personal data (name, address, sex, age etc.) are inputted, or amended, according to block 44 in FIG. 3.

After initial consultation according to block 43, the patient is referred to a specific department, for instance to the radiology department of the hospital, according to block 45. According to block 46, it is checked whether it is necessary to obtain an image (X-ray, ultrasound, MRI etc.) for further diagnosis, and if yes, such image is taken according to block 47 by the respective modality, and this image is stored s, block 48 in FIG. 3. The MS computer 9 (FIG. 1) then assigns the exam result (image, finding etc.) to the specialist, e.g. a radiologist, who reads this information or generally who examines the patient, according to block 49, the latter also in the case that no imaging was necessary.

Thereafter, the physician dictates his report, thereby using the information already available in the system, as explained above. During this generation of the report, according to block 50 in FIG. 3, the physician follows a selected one of the available templates, wherein the selected template depends on the modality, diagnosis, image type etc.

This selection of a specific template is shown in FIG. 4 at block 501. In detail, this FIG. 4 shows the generation of the medical report, as referred to with block 50 in FIG. 3 in more detail. In particular, after selection of the specific template at block 501, it is referred to entering of personal data, of image information and of voice macros, the two latter data entries in combination with automatic insertion of code data, by block 502. It is to be noted here that in the electronic templates, the most important sections are marked clearly in accordance with a reporting solution, for instance as follows:

complaints
clinical statement
history
comparison
procedure details
technique
medications In addition to the template, the radiologist also uses pre-filled text blocks (voice macros) that can contain e.g. the following information (auto-texts):

MRI of the brain
  left lobe
  right lobe
  cerebral cortex
  frontal lobes
  . . .
CT of the spine
  general
  s1-s2
  l3-l5
  . . .
Chest X-Ray
  Lateral
  . . .
  PA
  . . .

Thereafter, it is questioned according to block 503 of FIG. 4 whether there are ambiguities in code data, and if yes, it is, according to block 504, checked whether on the basis of the personal data as inputted before, such ambiguities can be ruled out. For instance, taking the sex of the patient into consideration, a number of conditions (e.g. prostate cancer . . . ) can be excluded a priori so that perhaps possible ambiguities could be removed on the basis thereof. After this check of block 504, it is again checked whether there is still an ambiguity given, see block 505 in FIG. 4, and if so, then it is tried whether it is possible to delete such ambiguity—according to block 506 in FIG. 4—on the basis of a previous condition which could make it more likely than a specific actual condition and, accordingly, a specific code is true, whereas another code can then be discarded as less likely.

Then again, a check with respect to the presence of ambiguities is carried out at block 507, and if there is still an ambiguity, then the actual medical examination information is checked in an attempt to exclude a less likely code which would not be consistent with this actual medical exam, compare block 508 in FIG. 4.

Thereafter, again with reference to FIG. 3, the dictated medical report is transcribed and corrected according to block 51, and the final medical report is signed by the physician according to block 52. The final report 18 (s. FIG. 1) is then ready for final coding processing, as described above.

The coding system 19 then uses all code information included in the medical reports 18, and if there are still ambiguities, these are identified and marked distinctly of clarification. A coding suggestion is made with varying certainties (x % likelihood) which can, for example, be color coded (e.g. green-likely; orange: medium etc.).

For instance, a medical report 18 generated in the manner as described above may have the following form:
GETWELL
MEMORIAL
HOSPITAL _____ DIAGNOSTIC IMAGING
500 W. Maple Maple Ave. Sometown, NY 12345-4423
555-1212-3434 Fax: 123-345-5678
ORD PHY: John V. Smith
DOB: 05/30/1943 AGE: 62 GENDER: F
Ordering Diagnosis: SCREENING MAMMO
CI #: 563134
Patient Name: Muster, Maria
SCREENING MAMMOGRAMS 06/15/2005 [C1]
CLINICAL HISTORY: 62-year old for a follow up screening procedure.
COMPARISON: None.
FINDINGS: Fibroglandular changes demonstrated of both breasts. The breast parenchy-mal pattern is irregular with areas of asymmetry in the left breast. Comparison with previous films is strongly recommended. [C2]
There are benign calcifications present in the right breast. The overlying skin and nipple regions are unremarkable.
IMPRESSION: Category 0 mammogram—Need additional imaging evaluation. [C3]
Note: Further correlation by means of physical exam is recommended since some cancers may be obscured by dense fibrocystic changes and occasionally can be missed on fatty infiltrated breasts. [C4]
  Robert M. Jones, MD
MT: ah
D: 6/15/2005 5:29:38 PM
Report ID: 12806

With [C1], hidden tags linked to embedded code data are referred to in the above example.

It should be noted that there is a number of modifications of the system and method as explained above. For instance, a hospital's computer system 1 may comprise all elements 2 to 16 of FIG. 1, and in fact also elements 19, 20, 21 and 23. As an alternative, a hospital's computer system may comprise only the elements 2 to 7 and 9, 10, 11, and the physician's system 12 to 16, together with a client system 8, may be present at another location, and may be connected to the hospital system via internet, or another network known in the art as LAN, WLAN or the like. The same applies with respect to the system for transcription and correction of the medical reports. In particular, it is of course possible that speech recognition takes place at a different place to which speech files are transmitted, in particular in digital form, for instance again via intranet or the like network. Furthermore, as already mentioned above, it is possible to immediately assign code data to the respective images or condition information, as taken; and however, it is also possible to assign such code data only at the place of the physician $D_1$ when calling in such condition information (for instance X-ray images) and viewing such condition information which may comprise a specific, individual identification which can be the basis for codes. Then, such code data can again automatically be assigned to this respective code information, compare the unit 14 in FIG. 1.

The invention claimed is:

1. A method for generating a medical report, said method comprising:
   receiving a selection of a template; and
   generating the medical report for a patient at least in part by:
      associating a preliminary set of medical billing codes with the medical report during generation of the medical report based, at least in part, on the selected template;
      receiving speech for entering information into a portion of the medical report corresponding to at least one section in the selected template,
      invoking a voice macro based, at least in part, on at least a portion of the received speech, wherein the voice macro has one or more first medical billing codes embedded in the voice macro, and wherein the voice macro, when invoked, instructs at least one processor to:
         enter predetermined text associated with the voice macro into the portion of the medical report, and
         update the preliminary set of medical billing codes by adding the one or more first medical billing codes to the preliminary set of medical billing codes to obtain an updated preliminary set of medical billing codes, wherein adding the one or more first medical billing codes to the preliminary set comprises automatically transferring the one or more first medical billing codes from the voice macro to the medical report by embedding the one or more first medical billing codes from the voice macro in the medical report,
      populating at least one field of the selected template with data associated with the patient obtained from one or more sources other than the received speech, and
      generating a processed set of medical billing codes that is at least a subset of the updated preliminary set of medical billing codes, wherein generating the processed set comprises:
         for at least one medical billing code of the updated preliminary set of medical billing codes, generating a determination of whether to retain the at least one medical billing code in the medical report, wherein generating a determination of whether to retain the at least one medical billing code comprises:

determining whether the at least one medical billing code represents at least one ambiguity in the updated preliminary set of medical billing codes, in response to a determination that the at least one medical billing code represents at least one ambiguity, determining whether the at least one ambiguity can be resolved based on the data obtained from the one or more sources other than the received speech, and in response to a determination that the at least one ambiguity can be resolved, resolving the at least one ambiguity using the data obtained from the one or more sources other than the received speech.

2. The method of claim 1, wherein:
resolving the at least one ambiguity using the data obtained from the one or more sources other than the received speech comprises resolving the at least one ambiguity based, at least in part, on previously stored personal data associated with the patient.

3. The method of claim 1, wherein:
resolving the at least one ambiguity using the data obtained from the one or more sources other than the received speech comprises resolving the at least one ambiguity based, at least in part, on previously stored condition information associated with the patient.

4. The method of claim 1, wherein:
resolving the at least one ambiguity using the data obtained from the one or more sources other than the received speech comprises resolving the at least one ambiguity based, at least in part, on medical examination information entered into the selected template.

5. The method of claim 1, wherein:
the processed set of medical billing codes are temporary medical billing code data, and
the method further comprises transforming the temporary medical billing code data to final medical billing code data based, at least in part, on a prescribed coding system for automatic billing.

6. The method of claim 1, further comprising:
in response to identifying one or more medical images associated with the medical report:
obtaining from data associated with the one or more medical images, one or more second medical billing codes linked to the one or more medical images, and
associating the one or more second medical billing codes with the medical report.

7. The method of claim 1, wherein the one or more sources other than the received speech comprises a source from which personal data, previous condition information, or previous examination information associated with the patient is obtained.

8. The method of claim 1, wherein the one or more sources other than the received speech comprises a source from which initial consultation and/or diagnosis data associated with the patient is obtained.

9. The method of claim 1, wherein the one or more sources other than the received speech comprises a source from which medical image information associated with the patient is obtained.

10. The method of claim 1, wherein associating the preliminary set of medical billing codes with the medical report during generation of the medical report comprises:
adding one or more second medical billing codes to the medical report, wherein adding the one or more second medical billing codes comprises embedding one or more second medical billing codes corresponding to at least one source of the one or more sources other than the received speech into the medical report.

11. A system comprising:
at least one processor; and
at least one storage device storing:
a plurality of templates;
at least one voice macro comprising a first voice macro, wherein the first voice macro is associated with text and one or more first medical billing codes, and wherein the first voice macro, when invoked, causes the at least one processor to enter at least some of the text associated with the first voice macro in a portion of a medical report and to associate at least some of the one or more first medical billing codes from the first voice macro with the medical report as hidden tags; and
executable instructions that, when executed by the at least one processor, cause the at least one processor to:
receive a selection of a template from among the plurality of templates stored by the at least one storage device;
associate a preliminary set of medical billing codes with the medical report for a patient during generation of the medical report based, at least in part, on the selected template;
receive speech for entering information into the portion of the medical report corresponding to at least one section in the selected template;
invoke the first voice macro based, at least in part, on at least a portion of the received speech to cause the at least one processor to enter the text associated with the first voice macro into the portion of the medical report and to associate the one or more first medical billing codes from the first voice macro with the medical report, wherein associating the one or more first medical billing codes comprises updating the preliminary set of medical billing codes by adding the one or more first medical billing codes to the preliminary set of medical billing codes in the medical report to obtain an updated preliminary set of medical billing codes;
populate at least one field of the selected template with data associated with the patient obtained from one or more sources other than the received speech; and
generate a processed set of medical billing codes that is at least a subset of the updated preliminary set of medical billing codes, wherein generating the processed set comprises:
for at least one medical billing code of the updated preliminary set of medical billing codes, generating a determination of whether to retain the at least one medical billing code associated with the medical report, wherein generating a determination of whether to retain the at least one medical billing code comprises:
determining whether the at least one medical billing code represents at least one ambiguity in the updated preliminary set of medical billing codes,
in response to a determination that the at least one medical billing code represents at least one ambiguity, determining whether the at least one ambiguity can be resolved based on the data obtained from the one or more sources other than the received speech, and in response to a determination that the at least one ambiguity can be resolved, resolving the at least one ambiguity using the data obtained from the one or more sources other than the received speech.

12. The system of claim 11, wherein:
resolving the at least one ambiguity using the data obtained from the one or more sources other than the received speech comprises resolving the at least one ambiguity based, at least in part, on previously-stored personal data associated with the patient.

13. The system of claim 11, wherein:
resolving the at least one ambiguity using the data obtained from the one or more sources other than the received speech comprises resolving the at least one ambiguity based, at least in part, on previously-stored condition information associated with the patient.

14. The system of claim 11, wherein:
resolving the at least one ambiguity using the data obtained from the one or more sources other than the received speech comprises resolving the at least one ambiguity based, at least in part, on medical examination information entered into the selected template.

15. A non-transitory computer-readable storage medium encoded with a plurality of computer-executable instructions that, when executed by at least one processor, cause the at least one processor to perform a method comprising:
associating a preliminary set of medical billing codes with a medical report for a patient during generation of the medical report;
receiving speech for entering information into a portion of the medical report,
invoking a voice macro based, at least in part, on at least a portion of the received speech, wherein the voice macro is associated with text and one or more first medical billing codes and wherein the voice macro, when executed by at least one processor, causes the at least one processor to:
enter at least some of the text associated with the voice macro into the portion of the medical report, and
associate at least some of the one or more first medical billing codes of the voice macro with the medical report, wherein associating at least some of the one or more first medical billing codes comprises updating the preliminary set of medical billing codes by adding the one or more first medical billing codes to the preliminary set of medical billing codes in the medical report to obtain an updated preliminary set of medical billing codes,
populating at least one field of the medical report with data associated with the patient obtained from one or more sources other than the received speech, and
generating a processed set of medical billing codes that is at least a subset of the updated preliminary set of medical billing codes, wherein generating the processed set comprises:

for at least one medical billing code of the updated preliminary set of medical billing codes, generating a determination of whether to retain the at least one medical billing code associated with the medical report, wherein generating a determination of whether to retain the at least one medical billing code comprises:
determining whether the at least one medical billing code represents at least one ambiguity in the updated preliminary set of medical billing codes,
in response to a determination that the at least one medical billing code represents at least one ambiguity, determining whether the at least one ambiguity can be resolved based on the data obtained from the one or more sources other than the received speech, and
in response to a determination that the at least one ambiguity can be resolved, resolving the at least one ambiguity using the data obtained from the one or more sources other than the received speech.

16. The non-transitory computer-readable storage medium of claim 15, wherein
resolving the at least one ambiguity using the data obtained from the one or more sources other than the received speech comprises resolving the at least one ambiguity based, at least in part, on previously-stored personal data associated with the patient and/or on previously stored condition information associated with the patient.

17. The non-transitory computer-readable storage medium of claim 15, wherein
resolving the at least one ambiguity using the data obtained from the one or more sources other than the received speech comprises resolving the at least one ambiguity based, at least in part, on medical examination information entered into the medical report.

18. The non-transitory computer-readable storage medium of claim 15, wherein adding the one or more first medical billing codes to the preliminary set of medical billing codes comprises embedding the one or more first medical billing codes from the voice macro in the medical report.

19. The non-transitory computer-readable storage medium of claim 18, wherein embedding the one or more first medical billing codes from the voice macro in the medical report comprises embedding the one or more first medical billing codes in the medical report as hidden tags.

20. The non-transitory computer-readable storage medium of claim 19, wherein embedding the one or more first medical billing codes in the medical report as hidden tags comprises embedding the one or more first medical billing codes such that the one or more first medical billing codes embedded in the medical report are not visible when the medical report is presented to a clinician in a display.

* * * * *